United States Patent
Stotz et al.

(10) Patent No.: US 12,377,256 B2
(45) Date of Patent: Aug. 5, 2025

(54) CARDIAC SUPPORT SYSTEM FLOW MEASUREMENT USING PRESSURE SENSORS

(71) Applicant: KARDION GMBH, Stuttgart (DE)

(72) Inventors: Ingo Stotz, Ditzingen (DE); Thomas Alexander Schlebusch, Renningen (DE)

(73) Assignee: Kardion GmbH, Stuttgart (DE)

( * ) Notice: Subject to any disclaimer, the term of this patent is extended or adjusted under 35 U.S.C. 154(b) by 965 days.

(21) Appl. No.: 15/734,003

(22) PCT Filed: Jun. 6, 2019

(86) PCT No.: PCT/EP2019/064784
§ 371 (c)(1),
(2) Date: Jun. 3, 2021

(87) PCT Pub. No.: WO2019/234153
PCT Pub. Date: Dec. 12, 2019

(65) Prior Publication Data
US 2021/0290933 A1    Sep. 23, 2021

(30) Foreign Application Priority Data
Jun. 6, 2018  (DE) .......................... 102018208862.4

(51) Int. Cl.
*A61M 60/816* (2021.01)
*A61M 60/148* (2021.01)
(Continued)

(52) U.S. Cl.
CPC ........ *A61M 60/148* (2021.01); *A61M 60/178* (2021.01); *A61M 60/216* (2021.01);
(Continued)

(58) Field of Classification Search
CPC .............. A61M 60/174; A61M 60/178; A61M 60/237; A61M 60/274; A61M 60/523;
(Continued)

(56) References Cited

U.S. PATENT DOCUMENTS 3,088,323 A   5/1963   Welkowitz et al.
4,023,562 A   5/1977   Hynecek et al.
(Continued)

FOREIGN PATENT DOCUMENTS

CA   3 122 415     7/2020
CN   1192351 A    9/1998
(Continued)

OTHER PUBLICATIONS

Hertz Ph.D. et al., "Ultrasonic Engineering in Heart Diagnosis", The American Journal of Cardiology, Jan. 1967, vol. 19, No. 1, pp. 6-17.
(Continued)

*Primary Examiner* — Jon Eric C Morales
(74) *Attorney, Agent, or Firm* — Knobbe Martens Olson & Bear LLP

(57) ABSTRACT

The invention relates to an implantable vascular support system (10), comprising:—a fluid channel (13) passing through the support system (10) and through which fluid can flow; —a first pressure sensor (18a, b) arranged and configured to determine at least a static pressure or a total pressure in the region of the support system (10); —a second pressure sensor (17) arranged and configured to determine at least a static pressure or a total pressure in the region of the fluid channel (13).

10 Claims, 4 Drawing Sheets

(51) Int. Cl.
*A61M 60/178* (2021.01)
*A61M 60/216* (2021.01)
*A61M 60/274* (2021.01)
*A61M 60/546* (2021.01)
*A61M 60/554* (2021.01)

(52) U.S. Cl.
CPC ........ *A61M 60/546* (2021.01); *A61M 60/554* (2021.01); *A61M 60/816* (2021.01); *A61M 2205/0244* (2013.01); *A61M 2205/3351* (2013.01)

(58) Field of Classification Search
CPC ... A61M 60/531; A61M 60/81; A61M 60/816
See application file for complete search history.

(56) References Cited

U.S. PATENT DOCUMENTS

| | | |
|---|---|---|
| 4,559,952 A | 12/1985 | Angelsen et al. |
| 4,680,730 A | 7/1987 | Omoda |
| 4,781,525 A | 11/1988 | Hubbard et al. |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,865,759 A | 2/1999 | Koblanski |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,167,765 B1 | 1/2001 | Weitzel |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,010,954 B2 | 3/2006 | Siess |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,527,599 B2 | 5/2009 | Hickey |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,789,236 B2 | 10/2017 | Bonde |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |

(56) References Cited

U.S. PATENT DOCUMENTS

| | | |
|---|---|---|
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 12,178,554 B2 | 12/2024 | Stotz et al. |
| 12,179,009 B2 | 12/2024 | El Katerji et al. |
| 12,183,459 B2 | 12/2024 | Agnello et al. |
| 12,194,287 B2 | 1/2025 | Kassel et al. |
| 12,201,821 B2 | 1/2025 | Schlebusch et al. |
| 12,211,615 B2 | 1/2025 | Nix et al. |
| 12,222,267 B2 | 2/2025 | Stotz et al. |

(56) References Cited

U.S. PATENT DOCUMENTS

| | | |
|---|---|---|
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin et al. |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0172505 A1 | 7/2011 | Kim |
| 2011/0184301 A1 | 7/2011 | Holmstrom |
| 2011/0186943 A1 | 8/2011 | Pahl |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0197141 A1 | 8/2012 | Vanney |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289334 A1 | 10/2013 | Badstibner |
| 2013/0289376 A1 | 10/2013 | Lang |
| 2013/0303831 A1 | 11/2013 | Evans |
| 2013/0304404 A1 | 11/2013 | Dam |
| 2014/0005467 A1 | 1/2014 | Farnan et al. |
| 2014/0013852 A1 | 1/2014 | Brown et al. |
| 2014/0030122 A1 | 1/2014 | Ozaki |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0201900 A1 | 7/2015 | Syed |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0302672 A1 | 10/2016 | Kuri |
| 2016/0303299 A1 | 10/2016 | Muller |
| 2016/0317043 A1 | 11/2016 | Campo |
| 2016/0338629 A1 | 11/2016 | Doerr |
| 2017/0010144 A1 | 1/2017 | Lenner et al. |

(56) References Cited

U.S. PATENT DOCUMENTS

| | | |
|---|---|---|
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1* | 3/2018 | Nunez ............... A61M 60/816 |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0333059 A1 | 11/2018 | Casas |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |
| 2025/0032773 A1 | 1/2025 | Baumbach et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |

(56) References Cited

FOREIGN PATENT DOCUMENTS

| | | |
|---|---|---|
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| EP | 4 429 754 | 2/2025 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |

(56) References Cited

FOREIGN PATENT DOCUMENTS

| | | |
|---|---|---|
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

International Preliminary Report on Patentability and Written Opinion received in PCT Application No. PCT/EP2019/064784, dated Dec. 17, 2020 in 7 pages.

International Search Report and Written Opinion received in PCT Application No. PCT/EP2019/064784, dated Aug. 30, 2019 in 11 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

HeartMate 3™ Left Ventricular Assist System, Instructions for Use, Thoratec Corporation, Aug. 2017, pp. 536. [Uploaded in 3 parts].

* cited by examiner

CARDIAC SUPPORT SYSTEM FLOW MEASUREMENT USING PRESSURE SENSORS

BACKGROUND

Field

The invention relates to an implantable vascular support system, a method for determining at least a flow velocity or a fluid volume flow of a fluid flowing through an implanted vascular support system, and a use of two pressure sensors of an implantable vascular support system. The invention can in particular be used in (fully) implanted left ventricular assist devices (LVAD).

Description of the Related Art

Implanted left ventricular assist devices (LVAD) exist primarily in two design variants. The first are (percutaneous) minimally-invasive left ventricular assist devices. The second variant are left ventricular assist devices which are invasively implanted under an opening in the rib cage. The first variant conveys blood directly from the left ventricle into the aorta, because the (percutaneous) minimally invasive left ventricular assist device is positioned centrally in the aortic valve. The second variant conveys the blood from the left ventricle into the aorta via a bypass tube.

The task of a cardiac support system is to convey blood. The so-called cardiac output (CO, usually expressed in liters per minute) is of high clinical relevance here. Simply put, the cardiac output refers to the total volume flow of blood (out of a ventricle), in particular from the left ventricle to the aorta. The initial objective is therefore to obtain this parameter as a measured value during the operation of a cardiac support system.

Depending on the level of support, which describes the proportion of volume flow conveyed by a conveying means, such as a pump of the support system, to the total volume flow of blood from the ventricle to the aorta, a specific amount of volume flow reaches the aorta via the physiological path through the aortic valve. The cardiac output or the total volume flow ($Q_{CO}$) from the ventricle to the aorta is therefore usually the sum of the pump volume flow ($Q_p$) and the aortic valve volume flow ($Q_a$).

In the clinical setting, the use of dilution methods is an established procedure for determining the cardiac output ($Q_{CO}$). However, these dilutions methods all rely on a transcutaneously inserted catheter and can therefore only provide cardiac output measurement data during cardiac surgery. Whereas the determination of the cardiac output by a support system is difficult to implement, the pump volume flow ($Q_p$) can be determined by means of suitable components of the support system. For high levels of support, the aortic valve volume flow ($Q_a$) approaches zero or becomes negligibly small, so that $Q_p$ approximately equals CO or the pump volume flow ($Q_p$) can be used as an approximation for the cardiac output ($Q_{CO}$). Correlating the operating parameters of the support system, particularly the electrical power consumption, possibly supplemented by other physiological parameters, such as the blood pressure, is an established procedure for measuring the pump volume flow ($Q_p$).

Since these methods are based on statistical assumptions and the underlying pump characteristic map of the support system used, the correlated $Q_p$ can be error-prone. Increasing the measurement quality of the parameter $Q_p$ is therefore desirable.

SUMMARY

Based on this, the underlying object of the invention is to optimize an implantable vascular support system, in particular also with regard to the arrangement and the use of sensors.

Proposed here according to claim 1 is an implantable vascular support system comprising:
- a fluid channel, which passes through the support system and through which fluid can flow,
- a first pressure sensor, which is disposed and configured to determine at least a static pressure or a total pressure in the region of the support system,
- a second pressure sensor, which is disposed and configured to determine at least a static pressure or a total pressure in the region of the fluid channel.

The solution proposed here advantageously enables the calculation of the pump volume flow with the aid of pressure sensors integrated in the support system, in particular in the inlet cannula of the support system. The particularly advantageous aspect of the implementation using pressure sensors, in comparison with ultrasonic sensor systems, for example, is the low price, the small space requirement and the simple evaluation method.

The vascular support system is preferably a cardiac support system, particularly preferably a ventricular support system. The support system is routinely used to support the conveyance of blood in the circulatory system of humans, e.g. a patient. The support system can be disposed at least partially in a blood vessel. The blood vessel is the aorta, for example, in particular in the case of a left ventricular assist device, or the common trunk (truncus pulmonalis) into the two pulmonary arteries, in particular in the case of a right ventricular assist device. The support system is preferably disposed at the outlet of the left ventricle of the heart or the left ventricle. The support system is particularly preferably disposed in aortic valve position.

The support system is preferably a left ventricular cardiac support system (LVAD) or a percutaneous, minimally invasive left ventricular assist device. The support system is particularly preferably configured and/or suited to being disposed at least partially in a ventricle, preferably in the left ventricle of a heart, and/or in an aorta, in particular in aortic valve position.

The support system is furthermore preferably fully implantable. In other words, this means in particular that the means required for determination, in particular the pressure sensors, are located entirely inside the body of the patient and remain there. The support system can also have a multipart design, i.e. comprise a plurality of components that can be disposed spaced apart from one another, so that the pressure sensors and a processing unit (measuring unit), for example, can be disposed separated from one another by a wire. In the multipart design, the processing unit disposed separate from the pressure sensors can likewise be implanted or disposed outside the patient's body. Either way, it is not absolutely necessary for a processing unit to also be disposed in the body of the patient. For example, the support system can be implanted such that a processing unit (the support system) is disposed on the patient's skin or outside the patient's body and a connection to the pressure sensors disposed in the body is established. Fully implanted in this context means in particular that the means required for determination (here the pressure sensors) are located entirely inside the patient's body and remain there. This advantageously makes it possible to determine the pump volume flow even outside of cardiac surgery and/or estimate the cardiac output even outside of cardiac surgery.

The support system further preferably comprises a tube (or a cannula), in particular an inlet tube or inlet cannula, a flow machine, such as a pump, and/or an electric motor. The electric motor is a routine component of the flow machine. The (inlet) tube or the (inlet) cannula is preferably configured such that, in the implanted state, it can guide fluid from a (left) ventricle of a heart to the flow machine. The support system is preferably elongated and/or hose-like. The tube (or the cannula) and the flow machine are preferably provided in the region of oppositely disposed ends of the support system. The tube preferably forms or surrounds the fluid channel.

According to one advantageous configuration, it is proposed that a first pressure sensor be disposed in the region of an outer side of the support system. The first pressure sensor is preferably disposed in or on an outer side of an inlet cannula of the support system, which forms or surrounds the fluid channel.

According to one advantageous configuration, it is proposed that a first pressure sensor be disposed in or on a channel interior surface of the fluid channel. The fluid channel is preferably formed or surrounded by an inlet cannula of the support system.

According to one advantageous configuration, it is proposed that a second pressure sensor be disposed in or on a channel interior surface of the fluid channel. The first pressure sensor and the second pressure sensor are preferably disposed spaced apart from one another in or on a channel interior surface of the fluid channel.

According to one advantageous configuration, it is proposed that a first pressure sensor be disposed in the region of a first channel cross-section through which fluid can flow and the second pressure sensor be disposed in the region of a second channel cross-section through which fluid can flow different from the first channel cross-section through which fluid can flow. A first pressure sensor is preferably disposed in or on a channel interior surface of the fluid channel in the region of a or in a first (known) channel cross-section through which fluid can flow and a second pressure sensor is disposed in or on the channel interior surface of the fluid channel in the region of a or in a second (known) channel cross-section through which fluid can flow different from the first channel cross-section through which fluid can flow.

According to another advantageous configuration, it is proposed that at least the first pressure sensor or the second pressure sensor be implemented as a MEMS pressure sensor. MEMS stands for microelectromechanical system.

According to a further aspect, a method for determining at least a flow velocity or a fluid volume flow of a fluid flowing through an implanted vascular support system is proposed, comprising the following steps:
a) determining at least a static pressure or a total pressure in the region of the support system by means of a first pressure sensor,
b) determining at least a static pressure or a total pressure in the region of a fluid channel, which passes through the support system and through which fluid can flow, by means of a second pressure sensor,
c) determining at least the flow velocity or the fluid volume flow using the pressures determined in Steps a) and b).

In other words, the fluid volume flow relates in particular to a fluid volume flow which flows (only) through the support system itself, e.g. through an (inlet) tube or an (inlet) cannula of the support system. The fluid volume flow is furthermore preferably the volume flow of the fluid flowing through the fluid channel. The flow velocity is therefore in particular the flow velocity of the fluid flowing through the fluid channel.

This fluid volume flow is usually the so-called pump volume flow ($Q_p$), which quantifies only the flow through the support system itself. If this value is known in addition to the total volume flow or cardiac output ($Q_{CO}$), the so-called level of support can be calculated from the ratio of $Q_p$ to $Q_{CO}$ (i.e., $Q_p/Q_{CO}$). To determine the fluid volume flow, the obtained flow velocity can be multiplied, for example, with a cross-section of the support system through which fluid can flow, in particular a tube or cannula cross-section through which fluid can flow.

In Step c), the fluid volume flow can be determined based on Bernoulli's pressure equation for incompressible fluids, for example. The equation is:

$$p_t = p + \frac{\rho}{2} \cdot v^2 = const. \approx const.$$

In the above equation, $p_t$ is the total pressure, p is the static pressure, $\rho$ is the fluid density and v is the flow velocity. The equation therefore states that the total pressure $p_t$ consists of a static component and a kinematic component. For a flow with small, i.e. negligible, friction losses, this total pressure is constant and a velocity difference of the flow can therefore be calculated by measuring the pressure at two positions.

If the cross-sectional area A through which the fluid flows is furthermore known at each of these positions, the volume flow can be determined with the known fluid density $\rho$ using the continuity equation for incompressible fluids. The corresponding equation for the fluid volume flow Q is:

$$Q = \frac{A_2 \cdot \sqrt{\frac{2 \cdot \Delta p}{\rho}}}{\sqrt{1 - \left(\frac{A_2}{A_1}\right)^2}}$$

In Step c), the flow velocity can likewise be determined based on Bernoulli's pressure equation for incompressible fluids, for example. In this context, it is particularly advantageous if the first pressure sensor determines a static pressure and the second pressure sensor determines a total pressure. Since the pressure sensors are both integrated in or on the support system, it can be assumed that the static pressure measured by means of the first pressure sensor is also representative of the static pressure at the second pressure sensor. The flow velocity v can then be determined to:

$$v = \sqrt{\frac{2}{\rho} \cdot (p_t - p)}$$

For this purpose, the static pressure p is advantageously measured with the first pressure sensor and the total pressure $p_t$ is measured with the second pressure sensor.

According to one advantageous configuration, it is proposed that a static pressure be determined in Step a). A static pressure is preferably determined in both Step a) and in Step b).

According to one advantageous configuration, it is proposed that a total pressure in the region of the fluid channel be determined in Step b). Preferably, a static pressure is determined in Step a) and a total pressure is determined in Step b). In this case, the flow velocity v can be determined comparatively easily in Step c) according to the above equation.

Preferably, in Step a), at least a static pressure or a total pressure is determined in the region of a or in a first (known) channel cross-section of the support system through which fluid can flow, in particular the fluid channel, by means of the first pressure sensor. Further preferably, in Step b), at least a static pressure or a total pressure is determined in the region of a or in a second (known) channel cross-section of the support system through which fluid can flow, in particular the fluid channel, by means of the first pressure sensor.

According to one advantageous configuration, it is proposed that a flow cross-section of the fluid be changed between the steps a) and b). There is preferably a flow cross-sectional widening or a flow cross-sectional narrowing between the first pressure sensor and the second pressure sensor.

According to a further aspect, the use of two pressure sensors of an implantable vascular support system to determine at least a flow velocity or a fluid volume flow of a fluid flowing through the support system is proposed.

BRIEF DESCRIPTION OF THE DRAWINGS

The details, features and advantageous configurations discussed in connection with the support system can correspondingly also occur in the method and/or the use presented here and vice versa. In this respect, reference is made in full to the statements there for a more detailed characterization of the features.

The solution presented here as well as its technical environment are explained in more detail below with reference to the figures. It is important to note that the invention is not intended to be limited by the design examples shown. In particular, unless explicitly stated otherwise, it is also possible to extract partial aspects of the facts explained in the figures and to combine them with other components and/or insights from other figures and/or the present description. The figures show schematically.

DETAILED DESCRIPTION

The vascular support system is preferably a ventricular and/or cardiac support system or a cardiac support system. Two particularly advantageous forms of cardiac support systems are systems which are placed in the aorta, such as the one depicted in FIG. 1a, and systems which are placed apically, such as the one depicted in FIG. 1b.

Figure 1A:
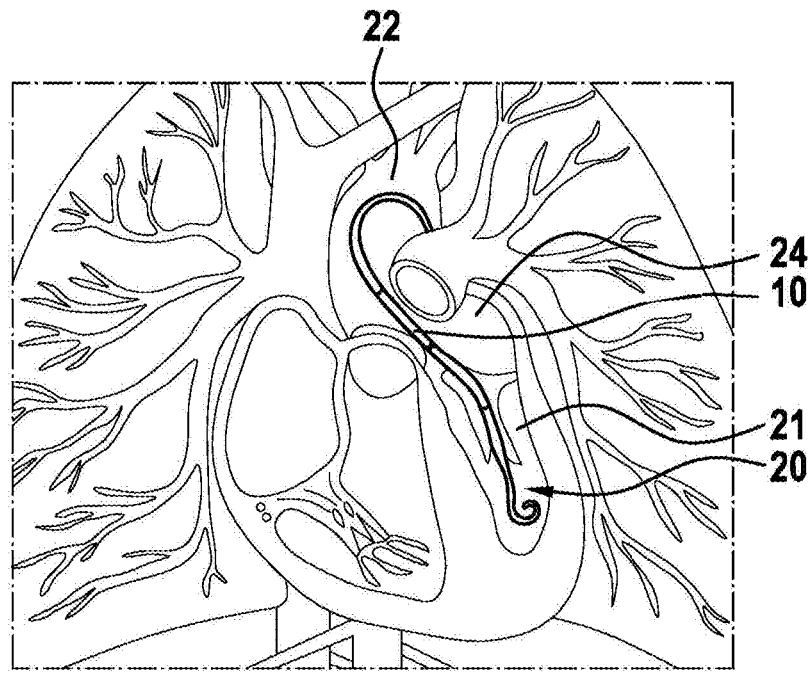
FIG. 1a: a percutaneous, minimally invasive left ventricular assist device.
Figure 1B:
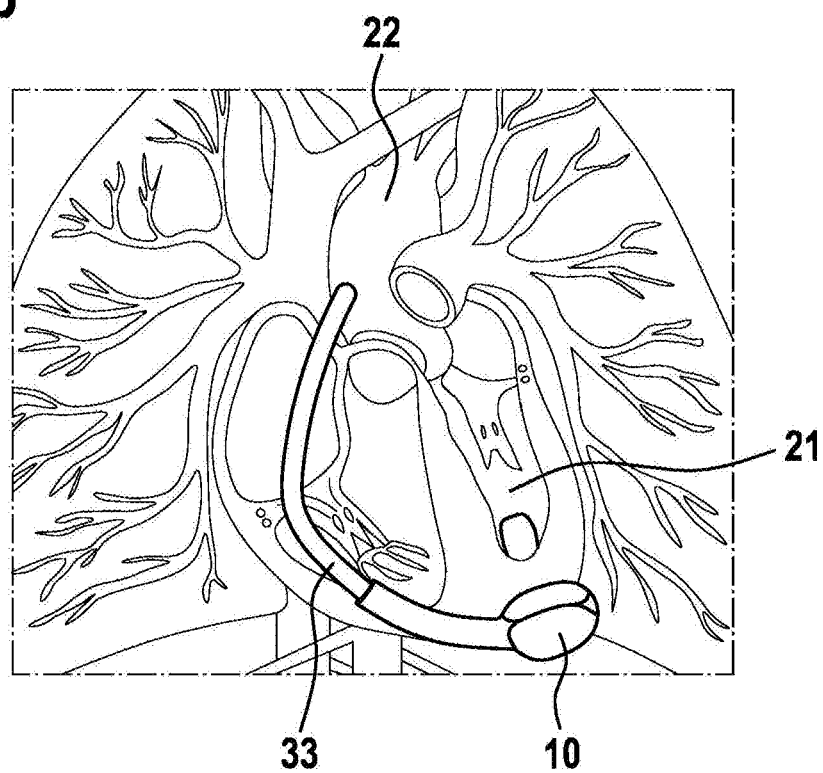
FIG. 1b: a left ventricular assist device invasively implanted under an opening in the rib cage.

The support system 10 is described in the following using a left ventricular assist device (LVAD) as an example. Implanted left ventricular assist devices (LVAD) exist primarily in two design variants, as shown in FIGS. 1b and 1b. FIG. 1a shows a (percutaneous) minimally invasive left ventricular assist device 10, whereas FIG. 1b shows a left ventricular assist device 10 invasively implanted under an opening in the rib cage. The variant of FIG. 1a conveys blood directly from the left ventricle 21 through the atrium 24 into the aorta 22, because the (percutaneous) minimally invasive left ventricular assist device 10 is positioned centrally in the aortic valve. The variant of FIG. 1b conveys the blood from the left ventricle 21 into the aorta 22 via a bypass tube 33.

Depending on the level of support, which describes the proportion of volume flow conveyed by a conveying means, such as a pump of the support system, to the total volume flow of blood from the ventricle 21 to the aorta 22, a specific amount of volume flow reaches the aorta 22 via the physiological path through the aortic valve. The cardiac output or the total volume flow ($Q_{CO}$) from the ventricle 21 to the aorta 22 is therefore usually the sum of the pump volume flow ($Q_p$) and the aortic valve volume flow ($Q_a$).

$$Q_{CO}=Q_p+Q_a$$

Figure 2:
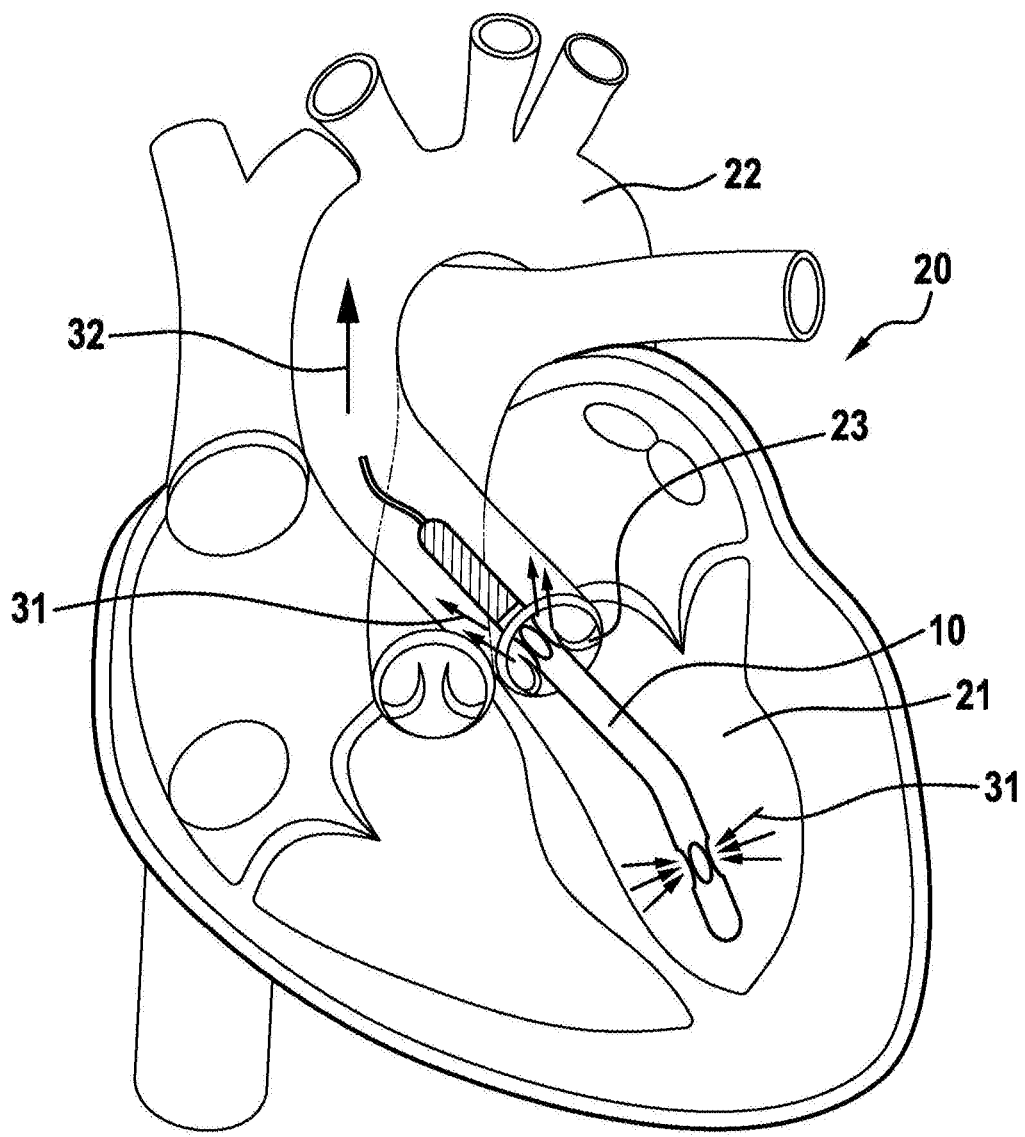
FIG. 2: an implanted vascular support system.

FIG. 2 schematically shows an implanted vascular support system 10. The cardiac support system 10 is implanted in a heart 20. The reference signs are used consistently, so that reference can be made in full to the above statements.

FIG. 2 shows a heart 20 with a minimally invasive cardiac support system (VAD pump) 10 as an example. The VAD is positioned centrally in the aortic valves 23 between the ventricle 21 and the aorta 22 and conveys a blood volume flow 31 from the ventricle 21 into the aorta 22 to support the cardiac output 32 of the patient.

Figure 3:
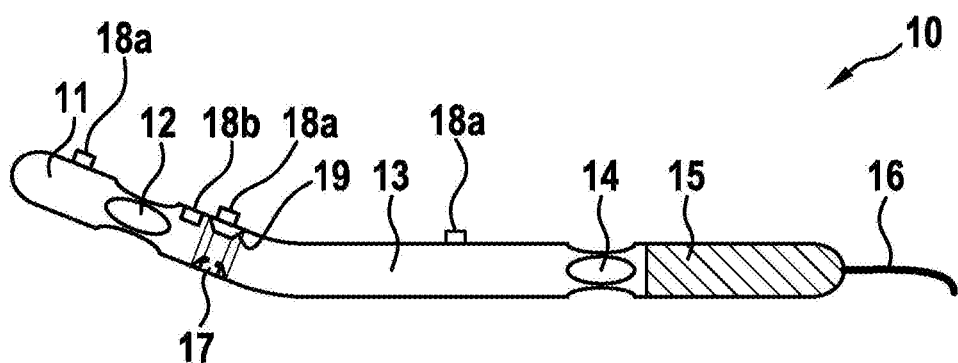
FIG. 3: the support system according to FIG. 2 in a detail view.

FIG. 3 schematically shows the support system 10 according to FIG. 2 in a detail view. The reference signs are used consistently, so that reference can be made in full to the above statements.

FIG. 3 schematically shows an implantable vascular support system 10 comprising:
a fluid channel 13, which passes through the support system 10 and through which fluid can flow,
a first pressure sensor 18a or 18b, which is disposed and configured to determine at least a static pressure or a total pressure in the region of the support system 10,
a second pressure sensor 17, which is disposed and configured to determine at least a static pressure or a total pressure in the region of the fluid channel 13.

According to the illustration of FIG. 3, as an example, the support system 10 further comprises a tip 11, which can contain sensors (for example temperature, pressure), an inlet cage with openings 12 for drawing in a liquid (here: blood), an inlet cannula 13 for delivering the blood to a (not shown) pump element in an impeller cage 14 provided with an opening, from which the blood can again exit the inlet cannula 13. Connected to this, as an example, is a drive (electric motor) 15 and an electrical supply cable 16.

In order to be able to estimate the cardiac output, the blood volume flow 31 through the inlet cannula 13 of the support system 10, which is also referred to as the so-called pump volume flow (symbol $Q_p$), is to be measured here. For this purpose, it is proposed here that two pressure sensors 17 and 18a/18b be integrated in or on the support system 10.

In Configuration A, the first pressure sensor 18a is positioned on the outside of the support system or the VAD pump 10, preferably in a region with a negligible flow velocity, e.g. on the outside of the tip 11, on the outside of a constriction 19 or on the outside of the inlet cannula 13. In other words, this means in particular that, in Configuration A, the first pressure sensor 18a is disposed in the region of an outer side of the support system 10.

Figure 4:
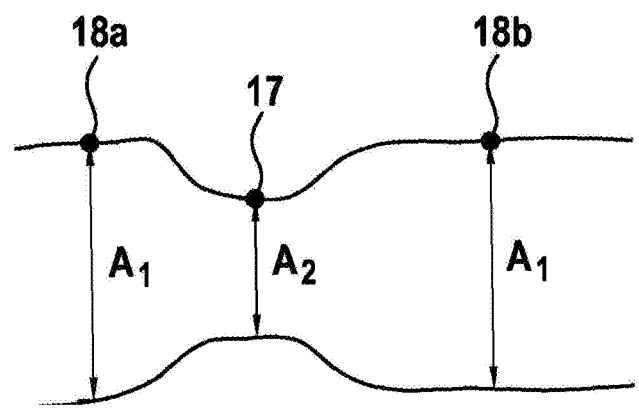
FIG. 4: an illustration of a fluid channel through which fluid can flow.

In Configuration B, the positioning of the first pressure sensor 18b differs as shown in FIG. 4. Here, the first pressure sensor 18b is seated inside the inlet cannula 13 at a position with a known flow cross-section $A_1$. In other words, this means in particular that, in Configuration B, the first pressure sensor 18b is disposed in or on a channel interior surface of the fluid channel 13.

In both Configurations A and B, another (second) pressure sensor 17 is used, which is disposed in or on a channel interior surface of the fluid channel (13). In FIG. 3, as an example, the second pressure sensor 17 is positioned in the inlet cannula 13 and preferably in an annular constriction 19 with the known flow cross-section $A_2$.

FIG. 3 according to Configuration B therefore also shows that a first pressure sensor 18b is disposed in or on a channel interior surface of the fluid channel 13 in the region of a first channel cross-section Ai through which fluid can flow and a second pressure sensor 17 is disposed in or on the channel interior surface of the fluid channel 13 in the region of a second channel cross-section $A_2$ through which fluid can flow different from the first channel cross-section through which fluid can flow.

The pressure measured by the pressure sensors 17 and 18a,b now depends on the flow velocity prevailing there. For a known fluid with a known density ρ, for a frictionless flow or a flow that has negligible losses between the pressure sensors, it follows that:

for Configuration A with the known cross-sectional area $A_2$ at the position of the second pressure sensor 17:

$$Q = A_2 \cdot \sqrt{\frac{2 \cdot \Delta p}{\rho}}$$

for Configuration B with the known cross-sectional areas $A_1$ at the position of the first pressure sensor 18a,b and $A_2$ at the position of the second pressure sensor 17:

$$Q = \frac{A_2 \cdot \sqrt{\frac{2 \cdot \Delta p}{\rho}}}{\sqrt{1 - \left(\frac{A_2}{A_1}\right)^2}}$$

For both configurations, the two pressure sensors 17 and 18a,b should preferably be positioned close to one another, because this can minimize any distortions in the result due to occurring pressure losses.

As an example, the first pressure sensor 18a,b and the second pressure sensor 17 are implemented as MEMS pressure sensors.

FIG. 4 schematically shows an illustration of a fluid channel through which fluid can flow. An equation for determining the fluid volume flow is derived below using the illustration of FIG. 4.

Based on Bernoulli's pressure equation for incompressible fluids. The equation is:

$$p_t = p + \frac{\rho}{2} \cdot v^2 = const. \approx const.$$

Equalizing the (constant) total pressure at two points 1,2, it follows that:

$$p_1 + \frac{\rho}{2} \cdot v_1^2 = p_2 + \frac{\rho}{2} \cdot v_2^2$$

This results in the pressure difference Δp:

$$\Delta p = p_2 - p_1 = \frac{\rho}{2} \cdot (v_1^2 - v_2^2)$$

The resulting constant mass flow is:

$$\dot{m} = \rho \cdot v \cdot A = const.$$

Solving for the flow velocity v, it follows that:

$$v = \frac{\dot{m}}{\rho \cdot A}$$

Substituting the flow velocity v in the equation for the pressure difference Δp results in:

$$\Delta p = \frac{\rho}{2} \dot{m}^2 \cdot \left(\left(\frac{1}{\rho \cdot A_1}\right)^2 - \left(\frac{1}{\rho \cdot A_2}\right)^2\right)$$

After a rearrangement, it follows that:

$$\dot{m} = \sqrt{\frac{\frac{2 \cdot \Delta p}{\rho}}{\left(\left(\frac{1}{\rho \cdot A_1}\right)^2 - \left(\frac{1}{\rho \cdot A_2}\right)^2\right)}}$$

After a rearrangement, it follows that:

$$\dot{m} = \frac{\rho \cdot A_2}{\sqrt{1 - \left(\frac{A_2}{A_1}\right)^2}} \cdot \sqrt{\frac{2 \cdot \Delta p}{\rho}}$$

A volume flow Q can be determined as a quotient of mass flow to density:

$$Q = \frac{\dot{m}}{\rho}$$

After substitution, the equation for determining the fluid volume flow is as follows:

$$Q = \frac{A_2}{\sqrt{1 - \left(\frac{A_2}{A_1}\right)^2}} \cdot \sqrt{\frac{2 \cdot \Delta p}{\rho}}$$

In the above derivation, Configuration A describes the limit case for $v_1$ tending to zero, which in the above equation A1 corresponds to tending to infinity.

Figure 5:
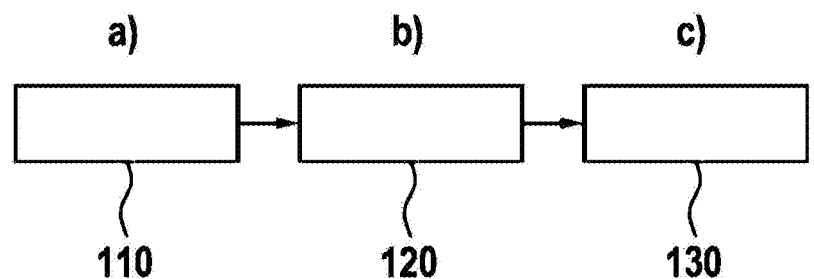
FIG. 5: a sequence of a method presented here in a routine operating sequence.

FIG. 5 schematically shows a sequence of a here presented method in a routine operating sequence. The method is used to determine at least a flow velocity or a fluid volume flow of a fluid flowing through an implanted vascular support system 10. The shown sequence of the method steps a), b) and c) with Blocks 110, 120 and 130 is only an example. Steps a) and b) in particular can also be carried out at least partially in parallel or even simultaneously. In Block 110, at least a static pressure or a total pressure in the region of the support system is determined by means of a first pressure sensor. In Block 120, at least a static pressure or a total pressure in the region of a fluid channel, which passes through the support system and through which fluid can flow, is determined by means of a second pressure sensor. In Block 130, at least the flow velocity or the fluid volume flow is determined using the pressures determined in Steps a) and b).

The solution presented here in particular enables one or more of the following advantages:

Continuous, accurate measurement of $Q_p$ using a system-integrated flow sensor. $Q_p$ is thus available as a control parameter of the support system, even outside the surgery scenario, with a quality comparable to that when using a CCO (Continuous Cardiac Output) thermodilution catheter.

When using pressure sensors, in particular MEMS pressure sensors, energy-efficient volume flow measurement is possible.

Compared to ultrasonic transducers, for example, a (MEMS) pressure sensor is very small.

The invention claimed is:

1. A cardiac support system comprising:
a fluid channel passing through the cardiac support system configured to permit fluid to flow therethrough;
a first pressure sensor configured to determine at least one of a static pressure or a total pressure in a first region of the cardiac support system having a first cross-sectional area; and
a second pressure sensor configured to determine at least one of a static pressure or a total pressure in a second region of the cardiac support system having a second cross-sectional area of a different size relative to the first cross-sectional area;
wherein:
the fluid channel has a longitudinal axis;
the cardiac support system has one or more side walls extending parallel to the longitudinal axis;
the first pressure sensor and the second pressure sensor are disposed on the one or more side walls; and
at least one of the first pressure sensor and the second pressure sensor is disposed on an outer side of the cardiac support system.

2. The cardiac support system of claim 1, wherein the first pressure sensor is disposed in the outer side of the cardiac support system.

3. The cardiac support system of claim 1, wherein the first pressure sensor is disposed in or on an interior surface of the fluid channel.

4. The cardiac support system of claim 1, wherein the second pressure sensor is disposed in or on an interior surface of the fluid channel.

5. The cardiac support system of claim 1, further comprising a first channel cross-section of the fluid channel through which fluid can flow and a second channel cross-section of the fluid channel through which fluid can flow, wherein an area of the second channel cross-section is different from an area of the first channel cross-section.

6. The cardiac support system of claim 1, wherein at least one of the first pressure sensor or the second pressure sensor is a MEMS pressure sensor.

7. A method for determining at least one of a flow velocity or a fluid flow volume of fluid flowing through a cardiac support system, the method comprising:
determining at least one of a first static pressure or a first total pressure in a region of the cardiac support system with a first pressure sensor;
determining at least one of a second static pressure or a second total pressure in a region of a fluid channel passing through the cardiac support system with a second pressure sensor;
determining at least one of a flow velocity or a fluid flow volume using at least one of the first static pressure, the first total pressure, the second static pressure, or the second total pressure; and
changing a flow cross-section of the fluid after determining at least one of a first static pressure or a first total pressure and before determining at least one of a second static pressure or a second total pressure.

8. The method of claim 7, wherein determining at least one of a first static pressure or a first total pressure comprises determining the first static pressure.

9. The method of claim 7, wherein determining at least one of a second static pressure or a second total pressure comprises determining the second total pressure.

10. A method for determining at least one of a flow velocity or a fluid flow volume of fluid flowing through a cardiac support system, the method comprising:
using two pressure sensors of a cardiac support system to determine at least one of a flow velocity or a volume flow of fluid flowing through the cardiac support system; and
changing a flow cross-section of the fluid after determining at least one of a first static pressure or a first total pressure and before determining at least one of a second static pressure or a second total pressure;
wherein the two pressure sensors are disposed along a sidewall of the cardiac support system.

* * * * *